US00PP08766P

United States Patent [19]

Zary

[11] Patent Number: Plant 8,766

[45] Date of Patent: Jun. 7, 1994

[54] MINIATURE ROSE PLANT NAMED 'JACMINNO'

[75] Inventor: Keith W. Zary, Thousand Oaks, Calif.

[73] Assignee: Bear Creek Gardens, Inc., Medford, Oreg.

[21] Appl. No.: 42,498

[22] Filed: Apr. 2, 1993

[51] Int. Cl.[5] ..... A01H 5/00

[52] U.S. Cl. ..... Plt./10

[58] Field of Search ..... Plt. 7.1, 10, 10.1, Plt. 28

*Primary Examiner*—Howard J. Locker

*Attorney, Agent, or Firm*—Klarquist Sparkman Campbell Leigh & Whinston

[57] ABSTRACT

A miniature rose having a dward, upright, well-branched and vigorous habit of growth; bright red flower color; ease of propagation by both softwood and hardwood cuttings; and bright, glossy, green, disease-resistant foliage.

1 Drawing Sheet

1

The present invention relates to a new and distinct variety of rose plant of the miniature class which was originated by me by crossing the variety JACibe, U.S. Plant Pat. No. 5,246, with the variety JACdew, U.S. Plant Pat. No. 5,122.

The primary objective of this breeding was to produce a new rose variety having the dwarf, compact habit and small flowers of the female parent combined with the vigor, disease resistance and flower color of the male parent. The objective was substantially achieved along with other desirable improvments as evidenced by the following unique combination of characteristics which are outstanding in the new variety and which distinguish it from its parents, as well as from all other varieties of which I am aware:

1. Dwarf, upright, well-branched and vigorous growth habit;
2. Disease-resistant, dark green, glossy foliage;
3. Small, bright red flowers with a lighter reverse; and
4. Ease of production from either softwood or hardwood cuttings.

Asexual reproduction of this new variety by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACibe, U.S. Plant Pat. No. 5,246.

*Pollen parent.*—JACdew, U.S. Plant Pat. No. 5,122.

Classification:

*Botanical.*—Rosa hybrida.

*Commercial.*—Miniature.

2

FLOWER

Observations made from specimens grown in a garden environment in Somis, Calif., from April through November, 1992.

Blooming Habit: Recurrent.

Bud:

*Size.*—½ inch when the petals start to unfurl.

*Form.*—Short, pointed ovoid.

*Color.*—When sepals first divide, bud color is Red Group 40A. When half blown, the upper sides of the petals are Red Group 40A; and the lower sides of the petals are Red Group 40A at the top of the petals, progressing to Red Group 40C at the base of the petals.

*Sepals.*—Color: Green Group 138B. Surface texture: Covered in fine hairs. There are three normally appendaged sepals. There are two unappendaged sepals with hairy edges.

*Receptacle.*—Color: Green Group 138B. Shape: Funnel. Size: Small (3/16×2/16 inch). Surface: Smooth.

*Peduncle.*—Length: Short (1–1¼ inches). Surface: Glandular. Color: Medium green and bronzy. Strength: Stiff, erect, slender.

Bloom:

*Size.*—Small. Average open size is 2 inches.

*Borne.*—Singly and several together, in flat clusters.

*Stems.*—Short (4–6 inches), strong.

*Form.*—When first open: High centered. Permanence: Flattens, all petals curl.

*Petalage.*—Number of petals under normal conditions: 20–25.

*Color.*—The upper side of the petals is Red Group 40A. The reverse side of the petals is Red Group 40A at the top of the petal, becoming constantly lighter red to Red Group 40C near the base of the petal. There is a large, yellowish half moon on both sides of each petal base (Yellow Group 4C). The major color on the upper side is Red Group 40 A.

*Variegations.*—Occasional white streak on petaloids.

*Discoloration.*—The general tonality at the end of the first day: No change. At the end of the third day: No change, but by day 5, there is a general fading of color to Red Group 40C or D.

*Fragrance.*—Slight.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Fair (5 days). As a cut flower: Fair (6 days).

Reproductive parts:

*Anthers.*—Size: Medium. Quantity: Many. Color: Yellow. Arrangement: Regular around styles, mixed with occasional petaloids.

*Filaments.*—Color: Yellow.

*Pollen.*—Color: Lemon yellow.

*Styles.*—Color: Red.

*Stigmas.*—Color: Red.

Form: Bush.

Growth: Vigorous, dwarf, upright, branching.

Foliage: Number of leaflets on normal mid-stem leaves: 5 or 7.

*Size.*—Small (3×2 inches).

*Quantity.*—Abundant.

*Color.*—New foliage: Reddish green. Old foliage: Dark green.

Leaflets:

*Shape.*—Pointed oval.

*Texture.*—Upper side: Glossy, smooth.

*Edge.*—Serrated.

*Serration.*—Single, small.

*Petiole rachis.*—Color: Green.

*Petiole underside.*—Rough, with prickles.

*Stipules.*—Short, serrated, bearded.

*Disease Resistance.*—Resistant to mildew and rust under normal growing conditions at Somis, Calif.

Wood:

*New wood.*—Color: Reddish green. Bark: Smooth.

*Old wood.*—Color: Green. Bark: Smooth.

Prickles:

*Quantity.*—On main canes from base: Ordinary. On laterals from main canes: Ordinary.

*Form.*—Medium, straight.

*Color when young.*—Red.

Small prickles:

*Quantity.*—On main stalks: Few. On laterals: Few.

*Color.*—Brown.

I claim:

1. A new and distinct variety of rose plant of the miniature class, substantially as herein shown and described, characterized particularly as to novelty by the unique combination of its dwarf, upright, well-branched and vigorous habit of growth; bright red flower color; ease of propagation by both softwood and hardwood cuttings; and bright, glossy, green, disease-resistant foliage.

* * * * *

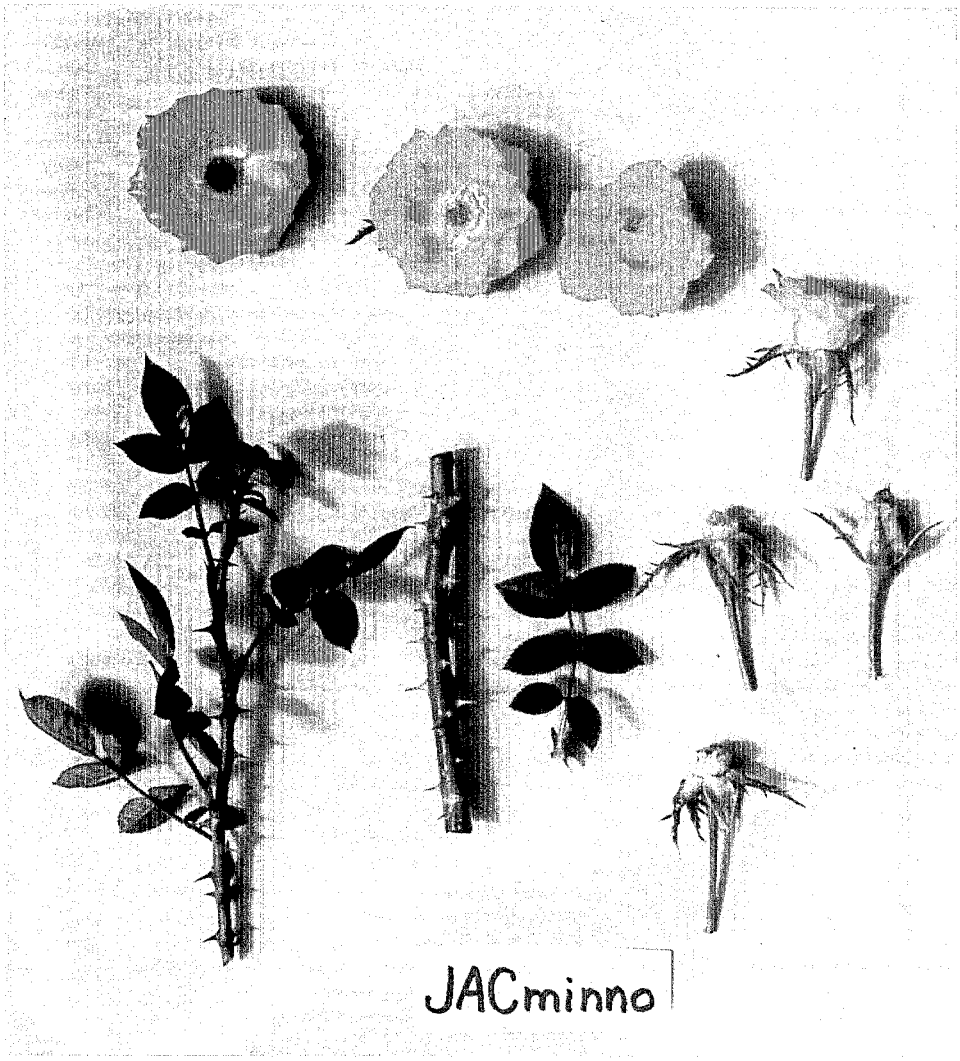
JACminno